United States Patent
Nakahara et al.

(10) Patent No.: US 7,166,753 B2
(45) Date of Patent: Jan. 23, 2007

(54) PROCESS FOR PRODUCTION OF HYDROGEN AND CARBONYL COMPOUNDS BY REACTING SUB- OR SUPER-CRITICAL WATER WITH ALCOHOLS

(75) Inventors: Koichi Nakahara, Osaka (JP); Kenzo Nagami, Osaka (JP); Okitsugu Kajimoto, Osaka (JP); Kazuya Kobiro, Kochi (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/510,972

(22) PCT Filed: Apr. 9, 2003

(86) PCT No.: PCT/JP03/04471

§ 371 (c)(1),
(2), (4) Date: Mar. 9, 2005

(87) PCT Pub. No.: WO03/086963

PCT Pub. Date: Oct. 23, 2003

(65) Prior Publication Data

US 2005/0154237 A1  Jul. 14, 2005

(30) Foreign Application Priority Data

| Apr. 12, 2002 | (JP) | 2002-111176 |
| Apr. 12, 2002 | (JP) | 2002-111177 |
| Aug. 7, 2002 | (JP) | 2002-229796 |
| Aug. 7, 2002 | (JP) | 2002-229797 |

(51) Int. Cl.
C07C 45/29 (2006.01)

(52) U.S. Cl. ..................... 568/383; 568/908

(58) Field of Classification Search ............ None
See application file for complete search history.

(56) References Cited

U.S. PATENT DOCUMENTS 6,180,845 B1 * 1/2001 Catallo et al. ............... 585/240
6,300,523 B1 * 10/2001 Ikushima et al. ........... 568/383

FOREIGN PATENT DOCUMENTS

| EP | 0 997 186 A1 | 5/2000 |
| JP | 09-188501 | 7/1997 |
| JP | 2979149 | 9/1999 |
| JP | 11-278801 | 10/1999 |
| JP | 11-279782 | 10/1999 |
| JP | 2000-136161 | 5/2000 |
| JP | 2000-143202 | 5/2000 |
| JP | 2000-239672 | 9/2000 |
| JP | 2002-088009 | 3/2002 |
| JP | 2002-105466 | 4/2002 |
| JP | 2003-063801 | 3/2003 |

* cited by examiner

Primary Examiner—Sikarl A. Witherspoon
(74) Attorney, Agent, or Firm—Ostrager Chong Flaherty & Broitman P.C.

(57) ABSTRACT

A process for producing a carbonyl compound involves allowing water to undergo phase transition to a supercritical or subcritical state in the presence of an alcohol compound so as to produce/generate water-derived hydrogen and at the same time convert the alcohol compound into a corresponding carbonyl compound. Specifically, the process is carried out by introducing the alcohol in a reaction tube along with water and heating and/or pressurizing the mixture of the alcohol and the water to bring the water into a subcritical or supercritical state. In this manner, water-derived hydrogen is produced and the alcohol is converted to a corresponding carbonyl compound. The process is preferably carried out in an oxygen-free environment.

13 Claims, 1 Drawing Sheet

PROCESS FOR PRODUCTION OF HYDROGEN AND CARBONYL COMPOUNDS BY REACTING SUB- OR SUPER-CRITICAL WATER WITH ALCOHOLS

TECHNICAL FIELD

The present invention relates to a production process of water-derived hydrogen, as well as a production process of carbonyl compounds, that takes advantage of subcritical or supercritical water. Specifically, the present invention relates to a production process of water-derived hydrogen in which alcohol compounds are reacted with subcritical or supercritical water. The present invention also relates to a novel production process of carbonyl compounds in which alcohol compounds are reacted with subcritical or supercritical water and converted into corresponding carbonyl compounds.

TECHNICAL BACKGROUND

When burned, hydrogen does not produce carbon dioxide, a notable greenhouse gas, and it ends up as water after it has released energy. For this reason, hydrogen has attracted the greatest attention as a source of clean energy. Traditionally, hydrogen has been produced from water by processes such as electrolysis of water, thermal decomposition of fossil fuels (e.g., heat decomposition of coal and reduction of water vapor by coal, oil, or gaseous hydrocarbons), and thermal decomposition of methanol.

However, the processes that rely on fossil fuels (e.g., oil, coal, and LNG) have limited future potential when the natural resources are in threat of being exhausted. In addition, these processes produce carbon monoxide and carbon dioxide along with hydrogen, and the resulting products contain significant amounts of impurities derived from fossil fuels. Thus, much effort has been put into developing processes for producing hydrogen from water, a material that does not pose any of these problems. However, only few water-based methods are available other than the electrolysis, including thermochemical decomposition, in which water is thermally decomposed at 800° C. or higher temperatures and which involves multiple chemical reactions known as the UT-3 cycle and IS process, and solar energy processes, which utilize photocatalysts or microorganisms. Many of these processes are still at the stage of basic research and have significant problems, such as very low yield and corrosion of the apparatuses.

Water in its subcritical or supercritical conditions exhibits different properties than when it is under normal conditions. By taking advantage of these properties, several production processes of hydrogen have been developed. These processes, however, are nothing more than the replacement of water in conventional water-based hydrogen production processes, which is used under normal temperature and pressure conditions, with subcritical or supercritical water.

For example, Japanese Patent Laid-Open Publication No. Hei 11-279782, entitled "Process for producing high-pressure hydrogen gas", describes a process in which water for electrolysis is subcritical or supercritical water. Japanese Patent Laid-Open Publication No. Hei 11-278801, entitled "Process for producing hydrogen gas", describes a process in which a high-pressure hydrogen gas is obtained by dispersing a light-scattering semi-conductor powder in subcritical or supercritical water and irradiating light to cause the water to decompose. Also, a production process of hydrogen is described in Japanese Patent No. 2979149 in which a carbon-containing substance is reacted with supercritical water at 600° C. or a higher temperature to cause the water to thermally decompose.

Conventional hydrogen-production processes involving the use of subcritical or supercritical water are based on the assumption that the reaction of the water with any organic compound is an oxidation reaction. These processes are therefore focused on the promotion of the oxidation of carbon atoms by water and each requires the use of a metal catalyst and supply of oxygen.

In fact, production process of hydrogen using subcritical or supercritical water is always associated with the generation of carbon dioxide, evidencing that the reaction is an oxidation process. One example is a process described in Japanese Patent Laid-Open Publication No. 2000-239672, in which a carbon source is reacted with subcritical or supercritical water to cause thermal decomposition and hydrolysis of the carbon source and to thereby give a light gas. This process requires collecting the carbon dioxide by-product. Another example is a proposal described in Japanese Patent Laid-Open Publication No. 2000-143202, which involves the use of a carbon dioxide absorbent. None of these approaches rely on a carbon dioxide-free reaction for hydrogen production.

The present inventors intensively studied the behavior of the atoms in water molecules in their subcritical or supercritical conditions and found that when water undergoes phase transition to the supercritical state in the presence of an alcohol compound, it produces water-derived hydrogen without generating carbon dioxide and the alcohol compound is predominantly converted into a corresponding carbonyl compound, rather than into a corresponding carboxylic acid.

In other words, the present inventors have found that a direct oxidation/reduction process can take place between an organic compound and subcritical or supercritical water.

This finding led the present inventors to devise the present invention.

Accordingly, the present invention in one aspect provides a process for effectively generating/producing water-derived hydrogen from supercritical water without generating carbon dioxide by-product.

In another aspect, the present invention provides a simple process for producing a carbonyl compound from an alcohol compound through a reaction of subcritical or supercritical water with the alcohol compound.

In known processes, an alcohol compound is converted to a carbonyl compound via oxidation of alcoholic hydroxyl groups into carbonyl groups. The oxidation process must be carefully controlled since strong oxidation may result in oxidative cleavage of the alcohol or generation of a carboxylic acid.

In carrying out these processes, the conditions for oxidation, including the types of the oxidizing agent and the solvent used and high temperature control, must be properly adjusted to avoid side reactions since the tendency of the alcoholic hydroxyl group to be oxidized varies depending on the type of the functional group adjacent to the carbon atom bearing the hydroxyl group. In addition, many of the oxidizing agents and the catalysts contain heavy metals and are difficult to handle.

The process of the present invention is characterized in that a carbonyl compound can be obtained from a corresponding alcohol compound without requiring the use of heavy metal oxidizing agents or catalysts and without undesirable side reactions.

DISCLOSURE OF THE INVENTION

As described, the first aspect of the present invention is a process for effectively generating/producing water-derived hydrogen from supercritical water without generating carbon dioxide by-product. Also, the second aspect of the present invention provides a process for producing a carbonyl compound in which an alcohol compound is converted into the carbonyl compound through a reaction of subcritical or supercritical water with the alcohol compound.

Specifically, the finding of the present inventors is that when water undergoes phase transition to a subcritical or supercritical state in the presence of a alcohol compound, one of the hydrogen atoms of the water molecule is combined with the hydrogen atom on the a-carbon of the secondary alcohol to form a hydrogen molecule ($H_2$). At the same time, one water molecule is formed and the alcohol compound is converted into a carbonyl compound. This reaction is different from what has been believed thus far and is represented by the following chemical equation:

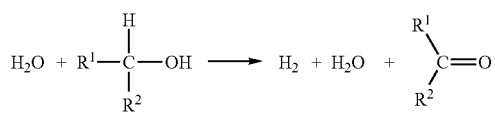

wherein, $R^1$ and $R^2$ each represent a hydrogen atom, or an alkyl group represented by $C_nH_{2n+1}$ with n being an integer of 1 to 6, a cycloalkyl group, or a phenyl group.

Accordingly, an essential aspect of the present invention comprises a process for producing a carbonyl compound in which water is allowed to undergo phase transition to a supercritical or subcritical state in the presence of an alcohol compound to produce/generate water-derived hydrogen and at the same time convert the alcohol compound into a corresponding carbonyl compound.

Specifically, the above process may be carried out by introducing the alcohol compound in a reaction tube along with water and heating and/or pressurizing the mixture of the alcohol compound and the water.

More specifically, the phase transition of the water to the supercritical or subcritical state may be carried out in an oxygen-free environment.

More specifically, the oxygen-free state may be established either by removing oxygen from the atmosphere in the reaction system, by using deoxygenated water, or by removing oxygen from the atmosphere in the reaction system while using deoxygenated water.

The term "phase transition" as used herein is intended to mean a change of water from its liquid state (liquid phase) or gas state (gas phase) to a subcritical or supercritical state.

BEST MODE FOR CARRYING OUT THE INVENTION

Figure 1:
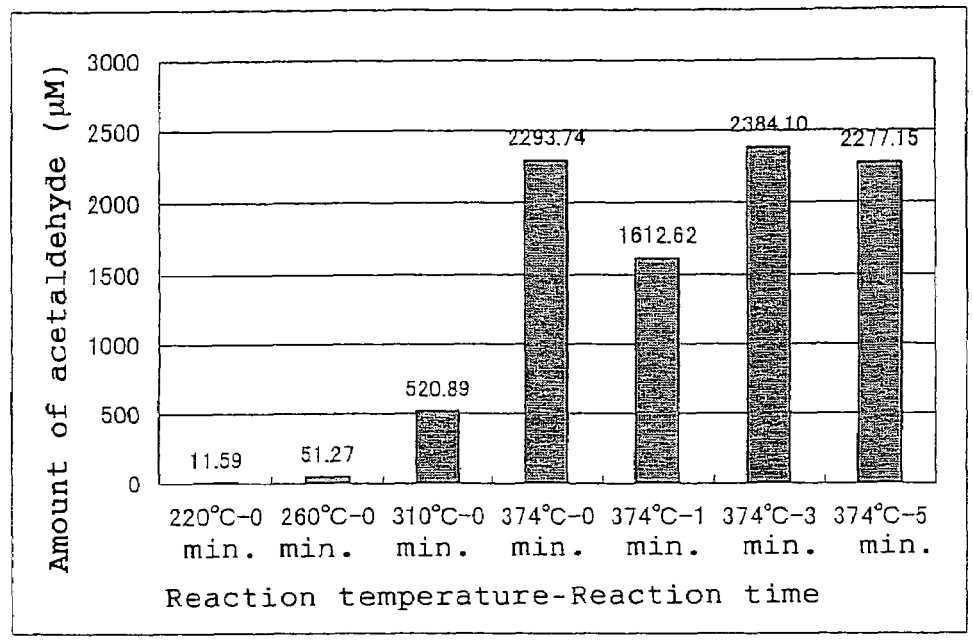
FIG. 1 is a graph showing the amount of acetaldehyde generated in Example 8 in which 1 mol/dm³ ethanol is reacted.

As described above, the present invention comprises a process for producing a carbonyl compound, in which water is allowed to undergo phase transition to a supercritical or subcritical state in the presence of an alcohol compound to generate/produce water-derived hydrogen and at the same time convert the alcohol compound into a corresponding carbonyl compound.

If a primary alcohol compound is used as the alcohol compound, then the phase transition of water to the subcritical or supercritical state results in the generation of water-derived hydrogen and conversion of the primary alcohol compound into an aldehyde, which may be thermally decomposed to produce carbon monoxide and carbon dioxide.

Thus, when it is desired to produce hydrogen, secondary alcohols are preferably used as the alcohol compound. The phase transition of water to the supercritical state in the presence of a secondary alcohol may be carried out by, for example, placing the secondary alcohol and water in a reaction tube and heating and/or pressurizing the mixture.

In comparison, when it is desired to produce a carbonyl compound through conversion of the alcohol compound, a primary or secondary alcohol is reacted with subcritical or supercritical water. This reaction can be carried out by placing a primary or secondary alcohol and water in a reaction tube and heating and/or pressurizing the mixture.

When ethanol, a primary alcohol, is used, the resulting acetaldehyde is thermally decomposed to produce hydrogen, carbon dioxide or methane as the temperature of the subcritical or supercritical water is raised or the reaction time is increased. However, the amounts of these compounds are negligible relative to the amount of the resulting carbonyl compound.

Specifically, the water placed in the reaction tube can be brought into the supercritical state in any of the following manners since water has a critical temperature of 374° C. and a critical pressure of 22.1 MPa: by placing a predetermined amount of water in a sealed reaction tube and raising the temperature; by placing water in a reaction vessel the interior of which has been adjusted to a predetermined pressure and raising the temperature to the critical temperature or higher temperatures; or by placing water in a reaction vessel the interior of which has been adjusted to a predetermined temperature and raising the pressure to the critical pressure or higher pressures.

As used herein, the term "subcritical state" refers to a state in which the temperature is 300° C. or higher and lower than 374° C. and the pressure is 9.4MPa or higher and lower than 22.1 MPa. A subcritical state can be reached in a similar manner to that used to reach a supercritical state.

In producing hydrogen, it can also be produced by bringing water into a subcritical condition, although the reaction takes longer.

To establish a subcritical or supercritical condition, commercially available apparatuses for producing supercritical water or those for performing reactions with supercritical water may also be used.

The hydrogen or carbonyl compounds produced in the process of the present invention can be collected in the following manner: Hydrogen can be collected in the form of gaseous hydrogen after the reaction has completed and the system has been brought back to room temperature and atmospheric pressure; and the carbonyl compounds can be collected in the form of liquid or solid after the reaction has completed and the system has been brought back to room temperature and atmospheric pressure.

In the production process of the present invention, yields of the desired products can be increased for example by carrying out the reactions of subcritical or supercritical water in an oxygen-free environment.

Since oxygen exists in small amounts in the air inside the reaction tube and in the water used, it reacts entirely at an early stage after the water has reached a subcritical or supercritical state. Carbon dioxide is also produced in small amounts but immediately reacts with, and consumes, oxygen. This prevents further generation of carbon dioxide. However, when it is desired to further increase the yields of the reaction products, it is preferable to remove oxygen from the atmosphere in the reaction tube and deoxygenate the water used.

To remove oxygen from the atmosphere in the reaction tube, the atmosphere may be replaced with nitrogen. To remove oxygen from the water, nitrogen may be bubbled through the water to replace the oxygen. Commercially available vacuum apparatuses, including vacuum pumps, and the vacuum freeze-thaw technique may also be used.

EXAMPLES

The present invention will now be described in further detail.

Example 1

Reaction of 1 mol/dm$^3$ 2-propanol

A sealable quartz capillary tube (inner diameter=1.5 mm, wall thickness=0.6 mm) was used as a reaction tube. A 1 mol/dm$^3$ aqueous solution of 2-propanol was placed in the capillary tube. After the solution was completely deaerated by the freeze-thaw deaeration technique, the tube was sealed. Nitrogen-bubbled water was used to make the solution.

The sealed capillary tube was then placed in a 10 ml SUS316 stainless steel-made reactor containing approximately 4 ml water. The reaction vessel was then heated in an electric furnace. Since the temperature condition in the reactor was in equilibrium with the temperature condition in the capillary tube, the temperature of the capillary tube was monitored by a thermocouple (temperature detector) mounted on the reactor and heating was continued until the temperature reached 450° C. Given that the reaction time was the time that passed after the preset temperature was reached, the reaction vessel was taken out of the electric furnace after a predetermined time period and was immediately chilled on an ice bath. Subsequently, the reaction products in the capillary tube were collected and were subjected to quantification and identification.

The quantification was performed by HPLC, GC-MS, and LC-MS using standard substances. The identification was performed by GC-MS, LC-MS, and NMR measurements using standard substances. The results are shown in Table 1 below.

The concentration for each reaction product shown in Table 1 was determined as the concentration of the quantified amount of each reaction product in an amount of water used in the reaction.

The freeze-thaw deaeration technique consists of the following steps: 1) place a sample solution in a capillary tube under a high vacuum or atmospheric pressure and connect the tube to a diffusion pump via a valve; 2) freeze the sample solution inside the capillary tube in liquid nitrogen; 3) suck the atmosphere in the capillary tube with the connected diffusion pump; 4) close the valve and heat (or leave at room temperature) the sample solution in the capillary to thaw; and 5) open the valve to discharge (suck with the diffusion pump) the released gas while the solution was frozen. The steps 2) through 5) are repeated 5 to 10 times until gas is no longer released. When the sample solution no longer releases gas, a substantially complete oxygen-free state is established in which the pressure of the atmosphere in the capillary tube is 10$^{-8}$ atm or below and the sample solution contains gas at a concentration of 5×10$^{-9}$ mol/dm$^3$ or less.

TABLE 1

| Reaction Temperature | Reaction Time | Reaction product (μmol/dm$^3$) | | | |
|---|---|---|---|---|---|
| (° C.) | (min) | H$_2$ | Acetone | CO$_2$ | CO |
| 450 | 30 | 9976.4 | 13130.2 | 0.0 | 0.0 |

As can be seen from the results above, acetone and hydrogen (gas) were obtained as reaction products of the 1 mol/dm$^3$ aqueous solution of 2-propanol with acetone produced from the liquid phase and hydrogen from the gas phase. Acetone and hydrogen were produced at an approximately 1:1 ratio. Also, it was demonstrated that no other gas components including carbon monoxide and carbon dioxide were formed.

Example 2

Reaction of 1 mol/dm$^3$ 2-Propanol

Instead of the capillary tube, a 10 ml SUS316-made vessel was used as a reaction tube. 3.4 ml of a 1 mol/dm$^3$ aqueous solution of 2-propanol (0.34 g/cm$^3$) were placed in the SUS316 reaction tube. After the air in the headspace of the reaction tube was replaced with nitrogen, the tube was sealed. Nitrogen-bubbled water was used to make the solution. While the temperature of the solution was monitored by a thermocouple mounted on the SUS316 reaction tube, the reaction tube was heated until the temperature reached 450° C. The heating was carried out by placing the reactor in a molten salt bath. Given that the reaction time was the time that passed after the preset temperature was reached, the SUS316 reaction tube was taken out of the molten salt bath after a predetermined time period and was immediately chilled on an ice bath. Subsequently, the reaction products in the SUS316 reaction tube were collected and were subjected to quantification and identification. The quantification was performed by HPLC, GC-MS, and LC-MS using standard substances. The identification was performed by GC-MS, LC-MS, and NMR measurements using standard substances. The results are shown in Table 2 below.

The concentration for each reaction product shown in Table 2 was determined as the concentration of the quantified amount of each reaction product in an amount of water used in the reaction.

TABLE 2

| Reaction Temperature | Reaction Time | Reaction product (μmol/dm$^3$) | | | |
|---|---|---|---|---|---|
| (° C.) | (min) | H$_2$ | Acetone | CO$_2$ | CO |
| 450 | 30 | 7469.3 | 6349.2 | 0.0 | 0.0 |

Acetone and hydrogen gas were obtained as reaction products of the 1 mol/dm$^3$ aqueous solution of 2-propanol with acetone produced from the liquid phase and hydrogen gas from the gas phase. Acetone and hydrogen gas were produced at an approximately 1:1 ratio. Also, it was demonstrated that no other gas components such as carbon dioxide and carbon monoxide were formed.

Example 3

Reaction of 1 mol/dm$^3$ cyclohexanol

A 1 mol/dm$^3$ aqueous solution of cyclohexanol (0.34 g/cm$^3$) was placed in a similar reaction tube (capillary tube) to that used in Example 1. As in Example 1, the solution was subjected to the freeze-thaw deaeration process and the tube was sealed. A similar reactor to that used in Example 1 was used. While the temperature of the solution was monitored by a thermocouple mounted on the reactor, the reaction tube was heated until the temperature reached 450° C. The heating was carried out by placing the reactor in an electric furnace. Given that the reaction time was the time that passed after the preset temperature was reached, the reactor was taken out of the electric furnace after a predetermined time period and was immediately chilled on an ice bath. Subsequently, the reaction products in the capillary tube were collected and were subjected to quantification and identification. The quantification was performed by HPLC, GC-MS, and LC-MS using standard substances. The identification was performed by GC-MS, LC-MS, and NMR measurements using standard substances. The results are shown in Table 3 below.

The concentration for each reaction product shown in Table 3 was determined as the concentration of the quantified amount of each reaction product in an amount of water used in the reaction.

TABLE 3

| Reaction Temperature | Reaction Time | Reaction product (μmol/dm$^3$) | | | |
|---|---|---|---|---|---|
| (° C.) | (min) | H$_2$ | cyclohexanone | CO$_2$ | CO |
| 450 | 30 | 7263.2 | 9326.4 | 0.0 | 0.0 |

Hydrogen gas and cyclohexanone were obtained as reaction products of the 1 mol/dm$^3$ aqueous solution of cyclohexanol with hydrogen gas produced from the gas phase and cyclohexanone from the liquid phase. It was also demonstrated that neither carbon monoxide nor carbon dioxide was formed.

Example 4

Reaction of 1 mol/dm$^3$ Cyclohexanol

A 1 mol/dm$^3$ aqueous solution of cyclohexanol (0.34 g/cm$^3$) was placed in a similar SUS316-made reaction tube to that used in Example 2. After the air in the headspace of the reaction tube was replaced with nitrogen, the tube was sealed. Nitrogen-bubbled water was used to make the solution. While the temperature of the solution was monitored by a thermocouple mounted on the SUS316 reaction tube, the reaction tube was heated until the temperature reached 450° C. The heating was carried out by placing the reactor in a molten salt bath. Given that the reaction time was the time that passed after the preset temperature was reached, the SUS316 reaction tube was taken out of the molten salt bath after a predetermined time period and was immediately chilled on an ice bath. Subsequently, the reaction products in the SUS316 reaction tube were collected and were subjected to quantification and identification. The quantification was performed by HPLC, GC-MS, and LC-MS using standard substances. The identification was performed by GC-MS, LC-MS, and NMR measurements using standard substances. The results are shown in Table 4 below.

The concentration for each reaction product shown in Table 4 was determined as the concentration of the quantified amount of each reaction product in an amount of water used in the reaction.

TABLE 4

| Reaction Temperature | Reaction Time | Reaction product (μmol/dm$^3$) | | | |
|---|---|---|---|---|---|
| (° C.) | (min) | H$_2$ | cyclohexanoe | CO$_2$ | CO |
| 450 | 30 | 9875.3 | 11822.4 | 0.0 | 0.0 |

As can be seen from the results above, hydrogen gas was produced, but neither carbon monoxide nor carbon dioxide was formed.

Example 5

Reaction of benzhydrol

Reaction was carried out using a sealable quartz capillary tube (inner diameter=4.2 mm, wall thickness=0.8 mm) as a reaction tube. 271 μmol benzhydrol was placed in the capillary tube along with 0.34 ml water. As in Example 1, the solution was completely deaerated by the freeze-thaw deaeration technique and the tube was melt-sealed. Nitrogen-bubbled water was used to make the solution.

The sealed capillary tube was then placed in a 10 ml SUS316 stainless steel-made reactor containing approximately 4 ml water. The reaction vessel was then sealed. Since the temperature condition in the reactor was in equilibrium with the temperature condition in the capillary tube, the temperature of the capillary tube was monitored by a thermocouple (temperature detector) mounted on the reactor and heating was continued until the temperature reached 420° C. The heating was carried out by placing the reactor in a molten salt bath. Given that the reaction time was the time that passed after the preset temperature was reached, the reaction tube was taken out of the molten salt bath after a predetermined time period and was immediately chilled on an ice bath. Subsequently, the reaction products in the capillary tube were collected and were subjected to quantification and identification. The quantification was performed by GC using standard substances. The identification was performed by GC-MS and NMR measurements using standard substances. The results are shown in Table 5 below.

TABLE 5

| Reaction Temperature (° C.) | Reaction Time (min) | Reaction product (μmol) | | | | | |
|---|---|---|---|---|---|---|---|
| | | $H_2$ | Methane | $CO_2$ | CO | Benzophenone | Diphenylmethane |
| 420 | 60 | 2.43 | 0 | 0 | 0 | 17.6 | 13.0 |

Hydrogen gas, benzophenone, and diphenylmethane were obtained as reaction products of the mixture of benzhydrol and water with hydrogen gas produced from the gas phase and benzophenone and diphenylmethane from the liquid phase. It was also demonstrated that none of carbon monoxide, carbon dioxide, and methane was formed.

Example 6

Reaction of 1 mol/dm³ ethanol

A set of 10 ml SUS316 stainless steel-made reaction vessels were used as reaction tubes. A 1 mol/dm³ aqueous solution of ethanol was placed in each of the SUS316 reaction tubes. After the air in the headspace of each reaction tube was replaced with nitrogen, the tubes were sealed. Nitrogen-bubbled water was used to make each solution. While the temperature of the solution in each SUS316 reaction tube was monitored by a thermocouple (temperature detector) mounted on the reaction tube, the reaction tubes were heated in a molten salt bath until the temperatures of 400° C., 450° C., and 500° C. were reached, respectively. Given that the reaction time was the time that passed after a preset temperature was reached, each of the SUS316 reaction tubes was taken out of the molten salt bath after a predetermined time period and was immediately chilled on an ice bath. Subsequently, the reaction products in each reaction tube were collected and were subjected to quantification and identification.

The quantification was performed by HPLC, GC-MS, and LC-MS using standard substances. The identification was performed by GC-MS, LC-MS, and NMR measurements using standard substances. The results are shown in Table 6 below.

The concentration for each reaction product shown in Table 6 was determined as the concentration of the quantified amount of each reaction product in an amount of water used in the reaction.

As can be seen from the results shown in Table 6, hydrogen and acetaldehyde were produced as reaction products of the 1 mol/dm³ aqueous solution of ethanol with hydrogen produced from the gas phase and acetaldehyde from the liquid phase. While hydrogen and acetaldehyde were generated at any reaction temperature and reaction time, the generated acetaldehyde was thermally decomposed to form carbon monoxide and carbon dioxide at higher temperatures and prolonged reaction times.

Example 7

Reaction of 1 mol/dm³ ethanol

A 1 mol/dm³ aqueous solution of ethanol was placed in each of a set of reaction tubes (capillary tubes) similar to that used in Example 1. As in Example 1, the solutions were subjected to the freeze-thaw deaeration process and the tubes were sealed. A set of reactors similar to that used in Example 1 were used. While the temperature of the solution in each reactor was monitored by a thermocouple mounted on the reactor, the reactors were each heated in a molten salt bath until the temperatures of 400° C., 450° C., and 500° C. were reached. Given that the reaction time was the time that passed after a preset temperature was reached, each reactor was taken out of the molten salt bath after a predetermined time period and was immediately chilled on an ice bath. Subsequently, the reaction products in the capillary tube were collected and were subjected to quantification and identification.

The quantification was performed by HPLC, GC-MS, and LC-MS using standard substances. The identification was performed by GC-MS, LC-MS, and NMR measurements using standard substances. The results are shown in Table 7 below.

TABLE 6

| Reaction Temp. (° C.) | Reaction Time (min) | Reaction product (μmol/dm³) | | | | | | |
|---|---|---|---|---|---|---|---|---|
| | | $H_2$ | Methane | Ethane | $CH_3CHO$ | $CO_2$ | CO | Ethylene |
| 400 | 10 | 2019.0 | 4596.3 | 0.0 | 7596.5 | 0.0 | 0.0 | 0.0 |
| 400 | 30 | 9866.9 | 4210.4 | 0.0 | 8777.4 | 0.0 | 0.0 | 0.0 |
| 450 | 10 | 28341.0 | 4970.4 | 0.0 | 22700.0 | 0.0 | 0.0 | 0.0 |
| 450 | 30 | 36212.0 | 7780.2 | 556.0 | 27705.0 | 0.0 | 0.0 | 0.0 |
| 500 | 10 | 116830.0 | 24038.0 | 3875.6 | 72100.3 | 890.3 | 135.2 | 886.4 |
| 500 | 30 | 199780.0 | 107460.0 | 2553.1 | 65917.0 | 12399.0 | 6152.7 | 10581.6 |

The concentration for each reaction product shown in Table 7 was determined as the concentration of the quantified amount of each reaction product in an amount of water used in the reaction.

TABLE 7

| Reaction Temp. (° C.) | Reaction Time (min) | Reaction product (μmol/dm$^3$) | | | | | | |
|---|---|---|---|---|---|---|---|---|
| | | $H_2$ | Methane | Ethane | $CH_3CHO$ | $CO_2$ | CO | Ethylene |
| 400 | 10 | 505.7 | 155.9 | 0.0 | 259.4 | 0.0 | 0.0 | 0.0 |
| 400 | 30 | 1640.5 | 434.9 | 0.0 | 909.4 | 0.0 | 0.0 | 0.0 |
| 400 | 60 | 2555.2 | 359.5 | 0.0 | 1948.4 | 0.0 | 0.0 | 0.0 |
| 450 | 10 | 4811.5 | 408.2 | 0.0 | 3578.9 | 0.0 | 0.0 | 63.0 |
| 450 | 30 | 11915.6 | 358.1 | 10.0 | 7985.0 | 0.0 | 0.0 | 1968.8 |
| 450 | 60 | 29838.9 | 2423.8 | 1306.8 | 21607.5 | 1312.3 | 0.0 | 6594.4 |
| 500 | 10 | 21618.5 | 7888.0 | 788.0 | 15393.0 | 786.8 | 0.0 | 6087.7 |
| 500 | 30 | 67177.8 | 37859.9 | 6331.0 | 38161.0 | 15159.4 | 6068.9 | 12690.5 |
| 500 | 60 | 153074.5 | 127107.3 | 27686.3 | 30896.5 | 59280.9 | 20887.6 | 19179.7 |

As can be seen from the results shown in Table 7, acetaldehyde ($CH_3CHO$) and hydrogen gas were obtained as reaction products of the 1 mol/dm$^3$ aqueous solution of ethanol with acetaldehyde produced from the liquid phase and hydrogen gas from the gas phase. Acetaldehyde and hydrogen gas in a molten salt bath were produced at an approximately 1:1 ratio. Generation of methane and ethane was observed at 500° C. but not at the other temperatures. Some of the resulting methane and ethane is considered to be reductively generated because of the generated hydrogen gas.

Example 8

Reaction of 1 mol/dm$^3$ ethanol

A 1 mol/dm$^3$ aqueous solution of ethanol was placed in each of a set of SUS316-made reaction tubes similar to that used in Example 2 and the tubes were sealed. Although nitrogen-bubbled water was used to make the solution, the sealing was carried out under atmospheric pressure and the air inside the tube was not replaced with nitrogen. A set of reactors similar to that used in Example 2 were used. While the temperature of each solution was monitored by a thermocouple mounted on the reactor, the reaction tubes were heated until respective temperatures were reached. The heating was carried out by placing each reactor in a molten salt bath. Given that the reaction time was the time that passed after a preset temperature was reached, each reactor was taken out of the molten salt bath after a predetermined time period and was immediately chilled on an ice bath. The reaction time of 0 min. means that the reactor was taken out of the molten salt bath just when the preset temperature was reached and was immediately chilled on an ice bath. Subsequently, acetaldehyde, one of the reaction products produced in each reaction tube, was subjected to quantification and identification. The results are shown in FIG. 1 below.

The concentrations shown in FIG. 1 were each determined as the concentration of the quantified amount of acetaldehyde in an amount of water used in the reaction.

As can be seen from the results shown in FIG. 1, acetaldehyde was produced at 500 μmol/dm3 or higher concentrations even at a temperature of 310° C. and at reaction time of 0 min.

Example 9

Reaction of 1 mol/dm$^3$ 2-propanol

A 1 mol/dm$^3$ aqueous solution of 2-propanol was placed in each of a set of SUS316-made reaction tubes similar to that used in Example 2 and the tubes were sealed. Although nitrogen-bubbled water was used to make the solution,.the sealing was carried out under atmospheric pressure and the air inside the tube was not replaced with nitrogen. A set of reactors similar to that used in Example 2 were used. While the temperature of each solution was monitored by a thermocouple mounted on the reactor, the reaction tubes were heated until respective temperatures were reached. The heating was carried out by placing each reactor in a molten salt bath. Given that the reaction time was the time that passed after a preset temperature was reached, each reactor was taken out of the molten salt bath after a predetermined time period and was immediately chilled on an ice bath. The reaction time of 0 min. means that the reactor was taken out of the molten salt bath just when the preset temperature was reached and was immediately chilled on an ice bath. Subsequently, acetone, one of the reaction products produced in each reaction tube, was subjected to quantification and identification. The results are shown in FIG. 2 below.

Figure 2:
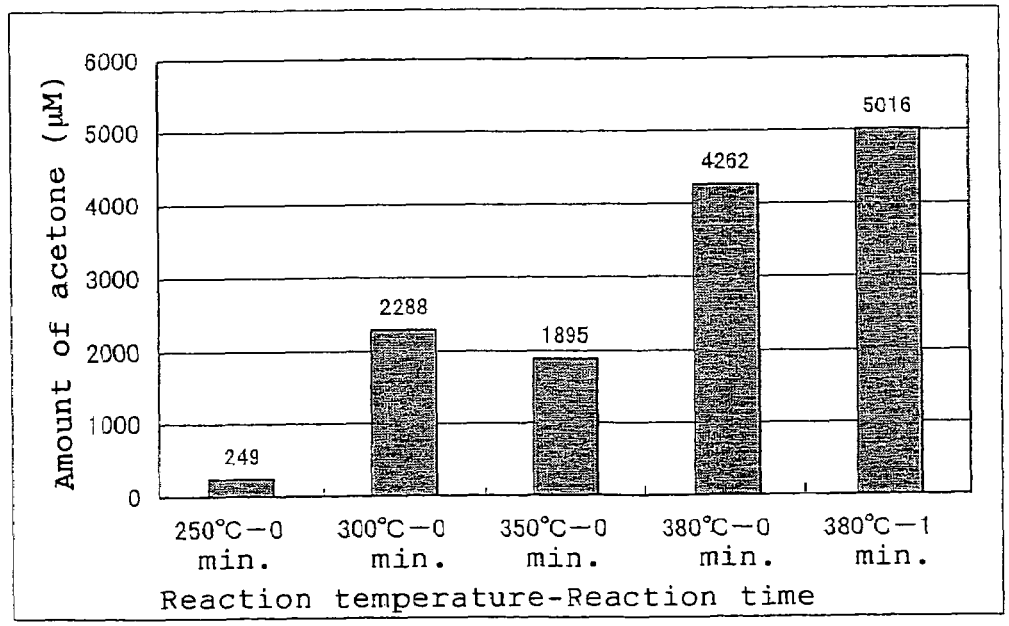
FIG. 2 is a graph showing the amount of acetone generated in Example 9 in which 1 mol/dm³ 2-propanol is reacted.

The concentrations shown in FIG. 2 were each determined as the concentration of the quantified amount of acetone in an amount of water used in the reaction. As can be seen from the results shown in FIG. 2, acetone was produced at approximately 2000 μmol/dm$^3$ at a temperature of 300° C. and at reaction time of 0 min.

Example 10

Reaction of benzhydrol

A 9.5 ml SUS316 stainless steel-made vessel was used as a reaction tube. 293 μmol benzhydrol was placed in the SUS316 reaction tube along with 3.5 ml of nitrogen-bubbled water (Conc.; 83.7 mmol/dm$^3$). After the air in the headspace of the reaction tube was replaced with nitrogen, the tube was sealed.

While the temperature of the solution in the SUS316 reaction tube was monitored by a thermocouple (temperature detector) mounted on the tube, the reaction tube was heated in a molten salt bath until a predetermined temperature was reached. Given that the reaction time was the time that passed after the preset temperature was reached, the SUS316 reaction tube was taken out of the molten salt bath after a predetermined time period and was immediately chilled on an ice bath. Subsequently, the reaction products in the reaction tube were collected and were subjected to quantification and identification.

The quantification was performed by GC using standard substances. The identification was performed by GC-MS and NMR measurements using standard substances. The results are shown in Table 8 below.

TABLE 8

| Reaction Temperature (° C.) | Reaction Time (min) | Reaction product ($\mu mol/dm^3$) | |
|---|---|---|---|
| | | Benzophenone | Diphenylmethane |
| 440 | 180 | 155.6 | 25.2 |

As can be seen from the results shown in Table 8, benzophenone was obtained as a reaction product of benzhydrol.

INDUSTRIAL APPLICABILITY

As set forth, the present invention provides a production process of hydrogen that allows direct production of hydrogen from water and thus does not require fossil resources. Also, the production process of the present invention does not generate carbon dioxide or carbon monoxide in producing hydrogen and therefore does not pose a threat to global warming.

In addition, the production process of the present invention consumes but at the same time generates water, so that there are no significant changes in the amount of water during the reaction and it is not necessary to add water to the reaction system. By incorporating a step for reducing the produced carbonyl compound to an alcohol, the process can be modified to continuously produce hydrogen, leading to potential applications in fuel cells or other energy sources.

Furthermore, the production process of the present invention allows efficient production of desired carbonyl compounds from primary alcohols and secondary alcohols by simply bringing water into subcritical or supercritical state. The process does not require control of other reaction conditions, nor does it require addition of special catalysts or oxidizing agents.

A further advantage of the production process of the present invention is that it can be applied to the processing of alcohol-containing exhaust gases since many of primary alcohols and secondary alcohols are volatile organic compounds. In such cases, the alcohols are converted to corresponding carbonyl compounds, facilitating their removal.

The invention claimed is:

1. A process for producing a carbonyl compound, comprising allowing water to undergo phase transition to a supercritical or subcritical state in the presence of an alcohol compound to produce/generate water-derived hydrogen and at the same time convert the alcohol compound into a corresponding carbonyl compound.

2. A process for generating water-derived hydrogen, comprising bringing water into a critical state in the presence of a secondary alcohol.

3. The process according to claim 2, wherein the process is carried out by introducing the secondary alcohol in a reaction tube along with water and heating and/or pressurizing the mixture of the alcohol and the water to bring the water into the supercritical state.

4. The process for producing hydrogen according to claim 2 or 3, wherein the phase transition of the water to the supercritical or subcritical state is carried out in an oxygen-free environment.

5. The process for producing hydrogen according to claim 4, wherein the oxygen-free state is established by removing oxygen from the atmosphere in the reaction system.

6. The process for producing hydrogen according to claim 4, wherein the oxygen-free state is established by using deoxygenated water.

7. The process for producing hydrogen according to claim 4, wherein the oxygen-free state is established by removing oxygen from the atmosphere in the reaction system while using deoxygenated water.

8. A novel process for producing a carbonyl compound, comprising reacting a primary or secondary alcohol with subcritical or supercritical water to produce/generate water-derived hydrogen and at the same time convert the alcohol into a carbonyl compound.

9. The process according to claim 8, wherein the process is carried out by introducing the primary or secondary alcohol in a reaction tube along with water and heating and/or pressurizing the mixture of the alcohol and the water to bring the water into the subcritical or supercritical state.

10. The novel process for producing a carbonyl compound according to claim 8 or 9, wherein the reaction of the primary alcohol or the secondary alcohol with the subcritical or supercritical water is carried out in an oxygen-free environment.

11. The novel process for producing a carbonyl compound according to claim 10, wherein the oxygen-free state is established by removing oxygen from the atmosphere in the reaction system.

12. The novel process for producing a carbonyl compound according to claim 10, wherein the oxygen-free state is established by using deoxygenated water as the water to be brought into the subcritical or supercritical state.

13. The novel process for producing a carbonyl compound according to claim 10, wherein the oxygen-free state is established by removing oxygen from the atmosphere in the reaction system while using deoxygenated water as the water to be brought into the subcritical or supercritical state.

* * * * *